US008709006B2

(12) United States Patent
Juergen et al.

(10) Patent No.: US 8,709,006 B2
(45) Date of Patent: Apr. 29, 2014

(54) SYSTEM AND METHOD FOR APPLYING PLASMA SPARKS TO TISSUE

(75) Inventors: Kolb F Juergen, Norfolk, VA (US); Scully Noah, Virginia Beach, VA (US); Schoenbach H Karl, Norfolk, VA (US); Dilip Paithankar, Natick, MA (US)

(73) Assignee: Old Dominion Research Foundation, Norfolk, VA (US)

( * ) Notice: Subject to any disclaimer, the term of this patent is extended or adjusted under 35 U.S.C. 154(b) by 984 days.

(21) Appl. No.: 12/759,853

(22) Filed: Apr. 14, 2010

(65) Prior Publication Data

US 2010/0280513 A1 Nov. 4, 2010

Related U.S. Application Data

(60) Provisional application No. 61/169,013, filed on Apr. 14, 2009.

(51) Int. Cl.
A61B 18/12 (2006.01)

(52) U.S. Cl.
USPC .......................................................... 606/34

(58) Field of Classification Search
USPC ............................................... 606/27, 34, 41
See application file for complete search history.

(56) References Cited

U.S. PATENT DOCUMENTS

| | | | | |
|---|---|---|---|---|
| 3,875,945 A | * | 4/1975 | Friedman | 606/45 |
| 3,884,237 A | * | 5/1975 | O'Malley et al. | 606/45 |
| 3,902,499 A | * | 9/1975 | Shene | 606/128 |
| 4,188,927 A | * | 2/1980 | Harris | 606/38 |
| 4,473,075 A | * | 9/1984 | Rexroth | 606/37 |
| 4,896,671 A | * | 1/1990 | Cunningham et al. | 600/374 |
| 5,009,656 A | * | 4/1991 | Reimels | 606/48 |
| 5,080,660 A | * | 1/1992 | Buelna | 606/45 |
| 5,152,768 A | * | 10/1992 | Bhatta | 606/128 |
| 5,300,068 A | * | 4/1994 | Rosar et al. | 606/34 |
| 5,395,363 A | * | 3/1995 | Billings et al. | 606/41 |
| 5,403,311 A | * | 4/1995 | Abele et al. | 606/49 |
| 5,454,809 A | * | 10/1995 | Janssen | 606/41 |
| 5,697,909 A | * | 12/1997 | Eggers et al. | 604/114 |
| 5,827,281 A | * | 10/1998 | Levin | 606/51 |
| 6,326,177 B1 | * | 12/2001 | Schoenbach et al. | 435/173.7 |
| 6,723,091 B2 | * | 4/2004 | Goble et al. | 606/41 |
| 6,813,515 B2 | * | 11/2004 | Hashimshony | 600/547 |

(Continued)

FOREIGN PATENT DOCUMENTS

| | | |
|---|---|---|
| WO | 2008/103777 A1 | 8/2008 |
| WO | 2009/137609 A2 | 11/2009 |

*Primary Examiner* — Michael Peffley
*Assistant Examiner* — Daniel Fowler
(74) *Attorney, Agent, or Firm* — Novak Druce Connolly Bove + Quigg LLP

(57) ABSTRACT

A pulse delivery system for producing a spark in tissue is disclosed. The system can include at least two electrodes having sharp surface features, where the at least two electrodes are electrically isolated from one another. The sharp features of the electrodes can be separated by a distance of about 2 to 20 mm. The system can also include a pulse generator for delivering pulsed voltage differences between the at least two electrodes. The pulsed voltage differences can producing a voltage difference ranging from about 2.5 kV to about 35 kV for a duration of about 50 ns to 3 μs. The system can include a controller for determining whether the plurality of pulsed voltage differences produced a spark between the at least two electrodes. A method of producing a spark in tissue for both therapeutic and cosmetic, i.e., non-therapeutic, applications is also disclosed.

14 Claims, 11 Drawing Sheets

(56) References Cited

U.S. PATENT DOCUMENTS

| | | | |
|---|---|---|---|
| 7,453,076 B2* | 11/2008 | Welch et al. | 250/492.3 |
| 8,000,813 B2* | 8/2011 | Schoenbach et al. | 607/154 |
| 2002/0058936 A1* | 5/2002 | Avrahami et al. | 606/41 |
| 2003/0153960 A1 | 8/2003 | Chornenky | |
| 2004/0236321 A1* | 11/2004 | Palanker et al. | 606/41 |
| 2005/0021015 A1* | 1/2005 | Keidar | 606/27 |
| 2005/0065510 A1 | 3/2005 | Carmel | |
| 2006/0257836 A1* | 11/2006 | Humphries et al. | 434/262 |
| 2006/0293649 A1* | 12/2006 | Lorang et al. | 606/32 |
| 2007/0179495 A1* | 8/2007 | Mitchell et al. | 606/41 |
| 2009/0062795 A1* | 3/2009 | Vakharia et al. | 606/52 |

* cited by examiner

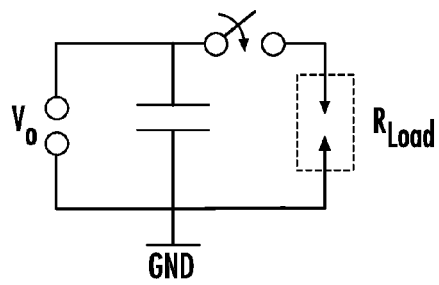
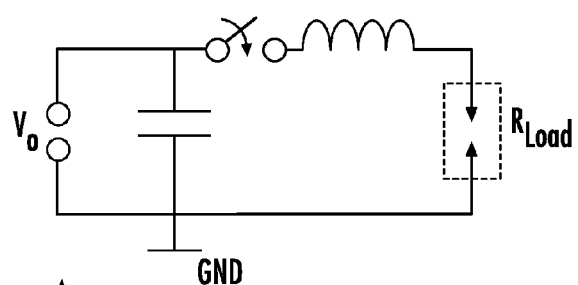
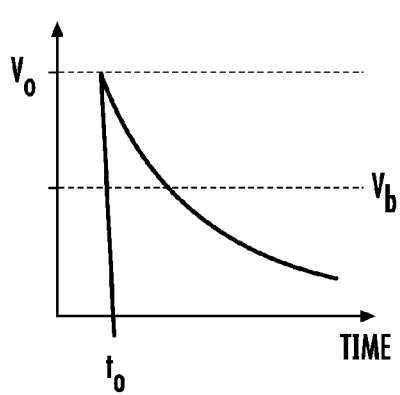
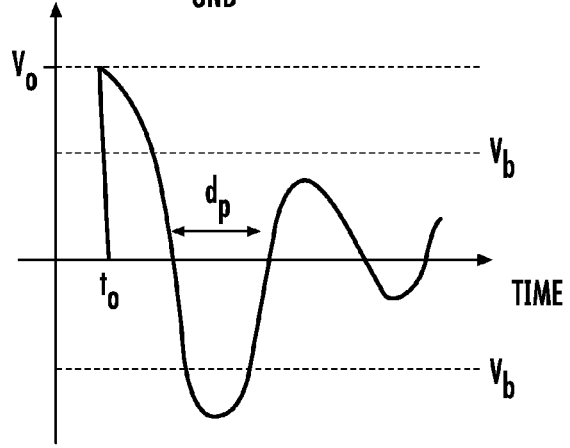
FIG. 12A
FIG. 12B
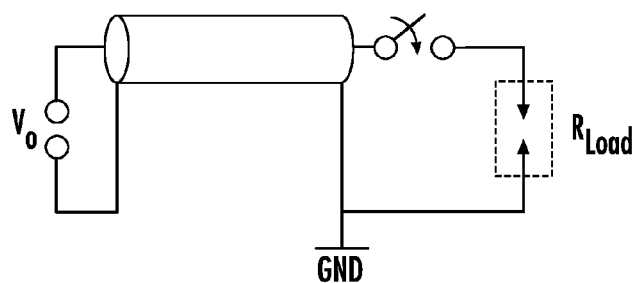
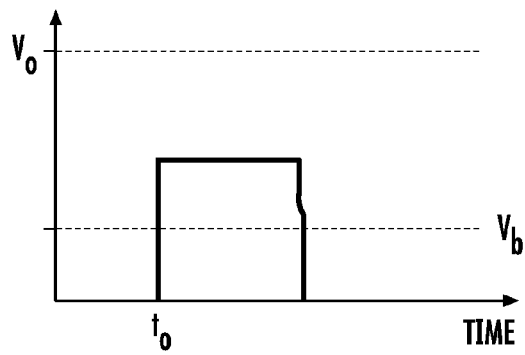
FIG. 12C

SYSTEM AND METHOD FOR APPLYING PLASMA SPARKS TO TISSUE

CROSS-REFERENCE TO RELATED APPLICATIONS

This application claims priority to U.S. Provisional Application No. 61/169,013, entitled "Method and System for Damaging and Cutting Tissue With Plasma Sparks," filed Apr. 14, 2009, the entirety of which is incorporated herein by reference.

BACKGROUND OF THE INVENTION

1. Technical Field

The present invention relates to a minimally invasive method for cutting, damaging and destroying selected cells or portions of tissue. More particularly, the present invention relates to the use of electrodes to create a plasma spark to cut, damage, and destroy cells or portions of selected tissue.

2. Related Art

The inventors have developed the present invention, which overcomes the drawbacks of prior art techniques and provides a new technique for cutting, damaging, ablating and destroying tissue that does not need to be carried out in a specialized medium, operates at low energy, and minimizes collateral damage to surrounding tissue.

Treating tissue using electrical discharge from an electrosurgical device has been the subject of investigation for many decades. This type of treatment has been used, for example, during standard open surgical procedures and procedures using probe-like devices that may be easily inserted into cavities and regions within a patient for minimally invasive procedures. Traditionally, the devices used in these techniques required the introduction of a conductive medium (either liquid or gas to generate a discharge). This requires relatively large incisions and use of circulated liquids or gases, which introduced further complications and risks. Previous devices and techniques have the potential to cause electrical burns to the tissue at the ground plate due to leakage currents. One reason for this problem is that most of the prior art devices used the tissue, e.g., skin, as the second electrode in the device.

An additional disadvantage of the prior art is that the tissue cuts were achieved by burning the tissue, which caused collateral damage to the surrounding tissue. The techniques disclosed in the prior art typically apply monopolar or biopolar radiofrequency energy. In monopolar applications electric current flows unpredictably and can produce unwanted tissue heating or stimulation. With conventional monopolar and bipolar electrosurgery techniques, high temperatures on the order of a few hundred degrees are reached with concomitant heating of surrounding tissue due to heat diffusion leading to collateral damage to surrounding tissue. In many electrically induced plasma based techniques, another medium such as saline solution is introduced near the target tissue. The addition of another medium, however, makes the procedure more cumbersome. It would be preferable if the tissue itself were to be cut without introduction of an external medium.

SUMMARY OF THE INVENTION

The invention is a new device and method for making precise cuts and incisions in tissue. The method can be used in a variety of applications to cut, damage, and/or destroy selected cells or portions of tissue. The possible applications where the device and method can be used are plentiful. Two examples include the removal of abnormal tissue, such as tumors and cancers, and non-therapeutic methods, such as the treatment of cellulite. The technology of the present invention could also be used as a minimally-invasive way to remove small glands or organs, such as tonsils, spleens, appendices, and others.

The device and method achieve a high level of precision through the generation of a spark discharge between at least two electrodes. Electrode configuration and distance determine the extent and location of the incision. Electrode separations can be as small as fractions of a millimeter and up to a centimeter or more (e.g., 3 centimeters). The spark originates from the sharpest tip or edge along these electrodes and along the shortest distance between the electrodes. This allows the design of minimally invasive systems that can be combined, for example, with a catheter to reach and treat internal organs. The system also permits the delivery of the spark with electrodes that penetrate through layers of tissue to the site that is to be treated.

The damage to the tissue, i.e., the cut, is controlled by the energy deposited by the spark. This energy can be regulated by the device that generates the spark. The damage to the tissue by the spark is caused by the rapid conversion and input of the available electrical energy into the tissue (i.e., the discharge medium). In the associated breakdown process, a rapidly expanding plasma channel is formed, which dissipates the energy through its explosive expansion. The damaged volume is determined by the radial range of the shock front, which extends to a distance where the energy per area is no longer sufficient to destroy cells.

To instigate the spark, it is necessary to apply a sufficiently high voltage for a long enough period to achieve dielectric breakdown of the tissue. 'Sufficiently high' and 'long enough' are determined by the electrode geometry and separation and the physical properties of the tissue. A controlled method to instigate the spark is the application of pulsed voltages where pulse shape and, in particular, pulse amplitude and duration can be adjusted.

The physical properties of cells and tissue being treated can be altered or conditioned by the application of electric pulses that facilitate the eventual formation of a spark. This tissue conditioning can be achieved by either repetitive application of the same pulsed voltage difference that is used to eventually initiate a spark or by applying pulsed voltage differences with specifically designed parameters. Tissue conditioning changes the dielectric properties of the tissue in a way that reduces the dielectric strength of the tissue and eventually allows the electrical pulses to produce a spark in the tissue. Tissue conditioning is not required if pulse duration and/or amplitude of the pulse used to instigate a spark discharge is long enough and/or high enough. However, tissue conditioning constitutes a practical method to achieve a spark under more relaxed conditions (i.e., with less intense parameters). As used herein, the term pulses and the phrases electrical pulses and pulsed voltage differences are all used interchangeably.

Desirably, the spark-plasma is created through delivery of electrical pulses and more desirably, through delivery of controlled electrical pulses with specific parameters. To control the parameters (e.g., pulse duration, pulse amplitude) of the delivered pulses and achieve breakdown conditions in the tissue, preferably a Pulse Forming Line ("PFL") or a Pulse Forming Network ("PFN") is used. As used herein, "breakdown" of tissue relates to production of a spark discharge, i.e., an ephemeral, localized plasma, produced between the electrodes.

PFLs and PFNs are circuits that can generate a single, rectangular voltage pulse across a load. The load can be matched or unmatched, although a single voltage pulse is only delivered when the load is matched. As used herein, a "matched load" is a load with an impedance equivalent to the impedance of the pulse source (e.g., PFL or PFN), whereas an "unmatched load" is a load, i.e., target tissue, with an impedance different than the impedance of the pulse source. The voltage pulse is created by the superposition of electromagnetic waves and their reflections (at the load and the terminations) that are propagating through the PFL or PFN once the wave is instigated. To launch a wave, one end of the circuit is shorted by a fast closing switch.

Generally, the medium for the wave propagation associated with the pulse generator is a continuous dielectric, such as found in coaxial cables, which are often used in a PFL. Use of cables in the PFL facilitates the generation of pulses having a desired duration. This is because, in a PFL, the pulse duration is determined by the length of the cable that is used and only cables of certain lengths are practical. The medium or cable associated with the pulse generator can be characterized by impedance and capacitance per unit length. Such an arrangement provides a fast rise time that approximates zero and can be as short as 1 nanosecond.

An alternative to using coaxial cables is use of a combination of capacitors and inductors in a PFN. The number and values of these discrete elements of capacitors and inductors can be chosen to generate similar pulses as from a PFL (such as pulse duration and energy) but often with a smaller and lighter system. The impedance of a PFL is determined by the specifications of the cable, whereas the impedance of a PFN can be chosen according to the requirements of the load and the elements of the PFN can be chosen to obtain the desired impedance. This impedance is related to the source impedance. Also, since the energy that is stored in the PFL or PFN is determined by its overall capacitance, it is further possible to modulate the energy that is delivered during a discharge (i.e., a spark) between the electrodes.

Pulse generators that include PFLs and PFNs can be configured in different ways. The concept of a Blumlein line or network (shown in FIGS. 6 and 8, respectively) allows a pulse to be delivered with an amplitude equivalent to the charging voltage, while a simple transmission line or network configuration (FIGS. 5 and 7, respectively) can only provide a pulse of half the charging voltage if the load is 'matched (i.e., if load impedance and system impedance values are the same). If the load impedance is mismatched to the source impedance, as shown in FIG. 9, a train of pulses with exponential decaying amplitudes will be delivered instead of a single pulse.

A mismatch occurs when the impedance of the load, e.g., tissue, does not equal the system impedance. The amplitude of the first pulse in the train is determined by how much system-impedance and load-impedance differ. If the load-impedance is lower than the system-impedance, as shown in FIG. 9(b), this amplitude will be lower than expected for the matched case. If the load-impedance is higher than the system impedance, as shown in FIG. 9(a) the amplitude will be higher and can reach a maximum of twice the charging voltage. The train of pulses that results in the case of a mismatched system does not affect the ability to damage and destroy tissue. However, the number of tissue conditioning pulses required in a mismatched system will be smaller than in a matched system.

The source impedance for the pulse generation system, e.g., Blumlein line-type PFL or PFN and Transmission line-type PFL or PFN, can be selected so that it is lower than the tissue impedance. A large impedance mismatch between the tissue and source gives rise to pulses with amplitudes of up to twice the charging voltage to be applied to the tissue. This may allow use of lower charging voltage pulse amplitudes to initiate a plasma spark.

A plasma spark can be generated under matched conditions by placing a resistor that is connected in parallel to a gap between the electrodes where the target tissue will be located. The resistor can be attached directly between the electrodes or between some other components in electrical communication with the respective electrodes. As long as the tissue impedance is higher than the resistor, the resistor will dominate the overall load resistance regardless of the value of the tissue impedance. In the case of a perfect match, the source impedance and the load impedance are equal. A resistor that produces a load impedance that is higher than the source impedance could be employed. This will lead to a higher voltage across the load than the input charging voltage. The peak voltage across the tissue load is a function of both the applied voltage and the resistor value and can be predicted by theoretical calculations, or appropriate simulation modeling software such as PSpice, or experimental measurements.

During the application of tissue conditioning pulses, the tissue impedance may gradually decrease. If the impedance of the pulse generator is not matched by a resistor in parallel to the treated tissue, the amplitudes of the train of pulses that are applied to the tissue will change accordingly. Generally, this will not affect the ability to damage the tissue with a spark. However, if the tissue impedance is initially much higher than the impedance of the pulse generator, pulse trains with amplitudes much higher than the charging voltage can be applied in order to produce tissue characteristics that enable breakdown faster than lower voltages. Alternately, by monitoring the pulse amplitudes, it is possible to compensate for this effect by changing the voltage that is used to charge the pulse generator during the exposure.

Unlike other media (gases, liquids), 'conditioning' using electrical pulses, may modify tissue conditions and facilitate spark formation during subsequent electrical pulses. As such these 'pre-plasma tissue conditioning pulses' are not themselves plasma pulses but eventually lead to the formation of plasma pulses. Tissue conditioning and spark discharges can be achieved by the same pulse generator system with either the same exposure parameters (amplitude, duration, repetition rate, number of pulses, different matching scenarios delivering closely spaced pulse trains) or a variation of these parameters during the treatment. However, for certain combinations of pulse duration and amplitude spark formation can occur even without any pre-plasma tissue conditioning pulses.

The dielectric strength of a homogeneous media, such as gases or liquids, depends on the electrode configuration and conditions, the value of the applied voltage and the duration of the voltage application. For the application of voltage pulses using a specific electrode configuration, the breakdown voltages, i.e., spark voltages, decrease with increasing pulse durations. While application of an electric pulse causes no lasting change of the composition and physical characteristics of a liquid or a gas unless a plasma forms, the application of an electric pulse to biological matter (cells or tissue) results in changes. In particular, the dielectric strength, which initially is closer to values known for liquids, is reduced by application of an electric pulse. After repetitive application of pulses, the dielectric strength of the biological matter approaches values that are closer to those of gases. Consequently, tissue conditioning pulses cause conditions in the biological material to become more favorable to the formation of a spark discharge. Hence, the repetitive application of a pulsed electric field will 'condition' the tissue for breakdown. The number of tissue conditioning pulses that are required to cause a plasma spark discharge will vary between different types of tissue and from tissue sample to tissue sample (whether from different subject or from different parts of the same subject).

When plasma formation occurs, the energy stored in the pulse delivery system is dissipated in the spark (with typical lifetimes on the order of several microseconds). High currents are observed. Current measurement or voltage measurement diagnostics tools can be built into the system disclosed herein to determine if the pulse was plasma-forming or non-plasma forming. The effect obtained in tissue can be controlled by choosing the number of plasma pulses delivered to tissue, including the number of pre-plasma tissue conditioning pulses.

Creation of a plasma spark in tissue leads to a clean and precise cut between the electrodes with minimal collateral damage. Applications include precision surgery, tissue cutting, sub-surface tissue-cutting, Subcision®-type treatments, and tissue ablation.

Another application is the treatment of cellulite. Septae that tether the skin to the fascia underlying the adipose tissue and the bulging adipose tissue are believed to be causes of the undesirable dimpling of skin, known as cellulite. These septae underneath or near a dimple can be cut and treated using the system and method disclosed herein in order to obtain visual improvement.

BRIEF DESCRIPTION OF THE DRAWINGS

FIG. 12a is a capacitive discharge unit.

FIG. 12b is a RCL discharge unit.

FIG. 12c is a Transmission line circuit.

DETAILED DESCRIPTION OF THE INVENTION

The following explanations are intended as an overview of different aspects relevant to the invention, such as electrode configuration, mechanisms of tissue damage and pulse delivery systems. They are by no means intended to be limited by the examples that are given and should be interpreted to demonstrate exemplary range of possibilities and embodiments of this invention.

Figure 1:
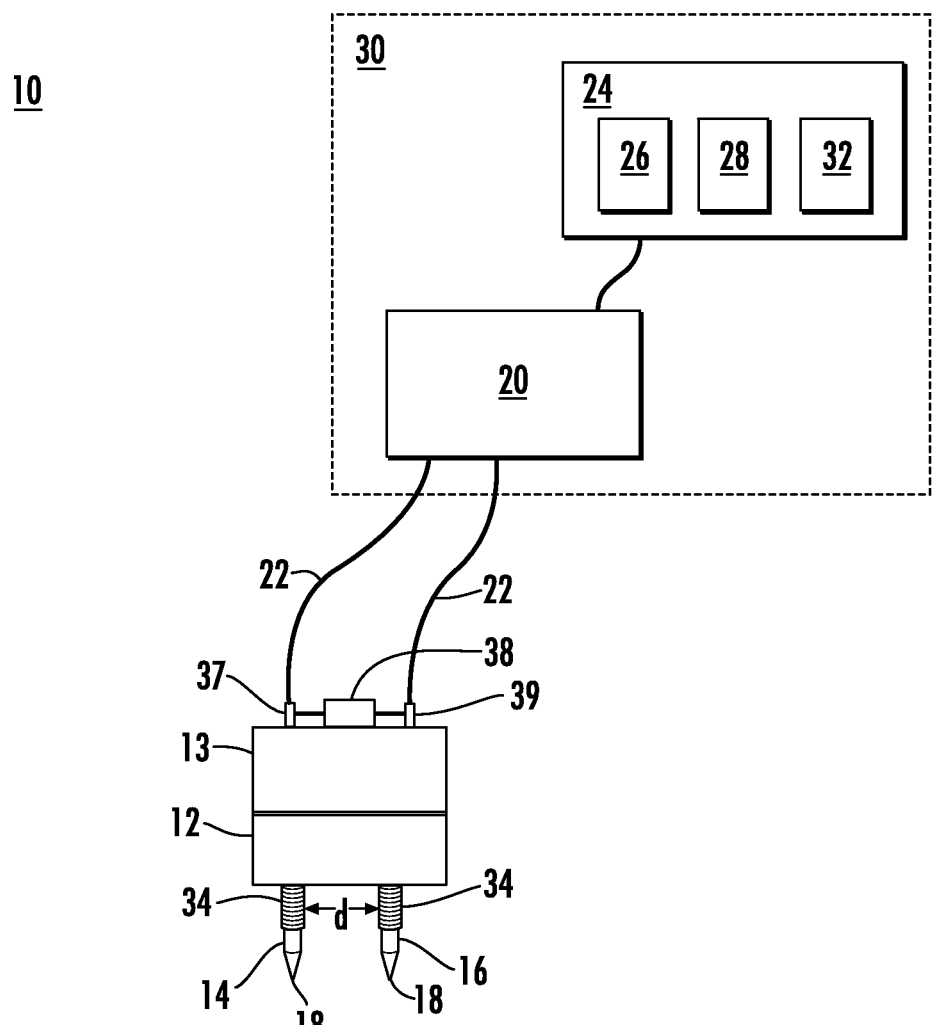
FIG. 1 is a schematic of a pulse delivery system according to the invention.

As shown in FIG. 1, the invention is drawn to a pulse delivery system 10. The pulse deliver system 10 can include an electrode head 12 that includes at least two electrodes 14, 16 having sharp surface features 18, wherein the at least two electrodes 14, 16 are electrically isolated and the sharp features 18 of the electrodes 14, 16 are separated by a distance (d) of about 2 to 20 mm. The system 10 can also include a pulse generator 20 in electrical communication with the at least two electrodes for delivering pulsed voltage differences between the at least two electrodes 14, 16. Electrical wires 22, e.g., insulated copper wires, can be used to connect the pulse generator with the electrodes 14, 16.

As used herein, the term "sharp surface features" is used to refer to edges, points, corners and other similar structures where one or more surfaces converge to form an angular interface. Exemplary sharp surface features 18 are shown in FIG. 11a-11f.

The electrode head 12 attached to a base 13, such as an elongated instrument. In some embodiments, the electrode head 12 can be disposable and the electrode head 12 and base 13 can be designed so the electrode head 12 can be removably attached to the base 13. Alternately, the electrode head 12 and the base 13 can be part of an integrated instrument. In some exemplary embodiments, the base 13 can be a handheld instrument, while in others the base 13 can be a catheter and the electrode head 12 can be attached to a distal end of the catheter 13.

The pulse generator 20 can generate pulsed voltage differences that produce a voltage difference ranging from about 0.5 kV to about 100 kV for a duration of about 1 ns to 30 µs. The voltage difference can be from 2.5 to 35 kV and the duration can be about 50 ns to 30 µs, or 50 ns to 1 µs in duration. One of the electrodes 14, 16 can be a ground electrode, while the voltage of the other electrode 16, 14 can be modulated to produce the desired voltage difference.

The system 10 can also include a controller 24 in electrical communication with the pulse generator 20, the electrodes 14, 16 or both. The controller 24 can include a processor 26 and a computer readable storage device 28. The computer readable storage device 28 can include machine executable instructions that, when executed, carry out a pulse application method.

The pulse generator 20, controller 24, processor 26 and computer readable storage device 28 can be separate or integrated into a single component or device. For example, the processor 26 and computer readable storage device 28 can be integrated onto a single chip. The controller 24 can include the chip comprising the processor 26 and computer readable storage device 28. In addition, the pulse generator 20 and controller 24 can be part of an integrated pulse generator/controller 30 (as shown by dashed box in FIG. 1).

As used herein, a "processor" is any form of electrical circuit or combination of electrical circuits capable of executing the computer readable instructions described herein. As used herein, a "computer readable storage device" can be any device capable of storing computer readable instructions. Exemplary computer readable storage devices 28 include, but are not limited to, hard drives, flash memory cards, DRAM, SDRAM, EPROM, EEPROM, disk drives, tape drives, and other forms of RAM and ROM memory.

The method stored on the computer readable storage device 28 can include instructions for causing the pulse generator 20 to deliver a plurality of pulsed voltage differences between the at least two electrodes 14, 16. While the pulsed voltage differences are being delivered, the instructions can cause the processor 26 can determine whether any of the plurality of pulsed voltage differences produced a spark between the at least two electrodes 14, 16.

The system 10 can also include a measuring device 32 in electrical communication with the electrodes 14, 16. The measuring device 32 can be a current measuring device or a voltage measuring device. The measuring device 32 can be separate from or incorporated into the controller 24 or the pulse generator 20. The current measuring device 32 can be any current measuring device, including, but not limited to, an ammeter, a multimeter, an oscilloscope, and a galvanometer. When a spark is not produced by a pulsed voltage difference, the current measuring device 32 will detect little or no current flowing, e.g., generally 10 mA or less, between the electrodes 14, 16. However, a significant current, generally exceeding 1 ampere, will be detected by the current measuring device 32 when a spark is formed between the electrodes 14, 16. The measuring device 32 can be any voltage measuring device including, but not limited to, a voltmeter, a multimeter, an oscilloscope or any other device similarly useful for measuring voltage.

The step of determining whether a spark was formed can include monitoring a current or voltage measured by the measuring device 32, and determining whether a spark was produced or not by comparing the measured current or voltage to a predetermined threshold value associated with spark formation. For example, if a measured current exceeds a predetermined value, such as 1 amp or more, it can be determined that a spark was formed. The value of the predetermined value will be determined by a variety of variables, e.g., resistance of the tissue and the electrical characteristics of the pulse generator.

Similarly, if a measured voltage difference between the electrodes drops to or below a predetermined value, it can be determined that a spark was formed. For example, if a 50 kV voltage difference is applied by the pulse generator, a spark may be detected if the voltage difference between the electrodes 14, 16 drops to 75% or less of the applied voltage difference (i.e., 37.5 kV or less), or 50% or less of the applied voltage difference (i.e., 25 kV or less).

After the controller 24 determines that a pulsed voltage difference produced a spark, the computer executable instructions can cause the system 10 to apply a predetermined number of additional pulsed voltage differences to the electrodes 14, 16. The voltage difference, the duration or both of the additional pulsed voltage differences (e.g., spark pulses) can be different from those of the plurality of pulsed voltage differences (e.g., tissue conditioning pulses). In this manner, the system 10 can apply a plurality of tissue conditioning pulses (i.e., the plurality of pulsed voltage differences), followed by the application of a plurality of sparking pulses (i.e., the additional pulsed voltage differences). Depending on the application, the sparking pulses can be for non-therapeutic, i.e., cosmetic, or therapeutic purposes.

Figure 5A:
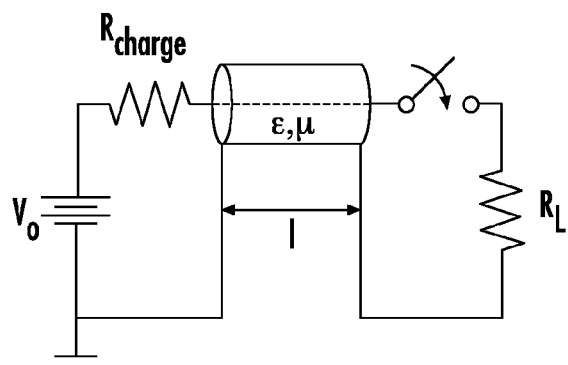
FIG. 5a is a schematic of a Transmission line-type PFL.
Figure 5B:
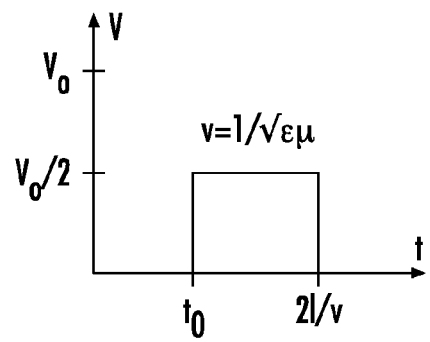
FIG. 5b is an example of a waveform for a Transmission line-type PFL.
Figure 6A:
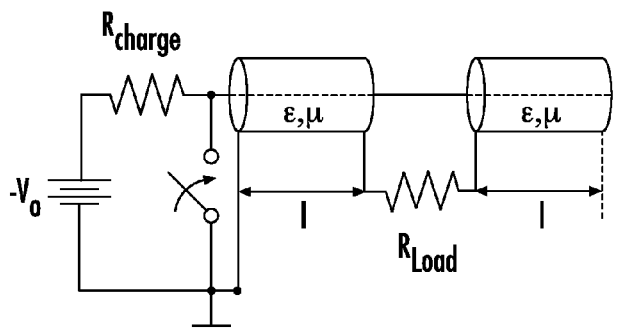
FIG. 6a is a schematic of a Blumlein line-type PFL.
Figure 6B:
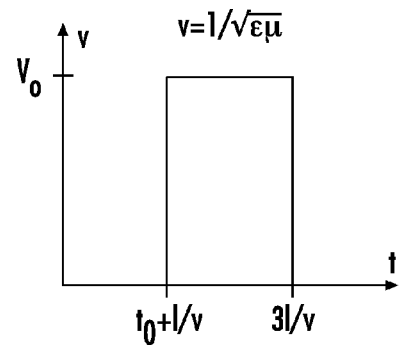
FIG. 6b is an example of a waveform for a Blumlein line-type PFL.
Figure 7A:
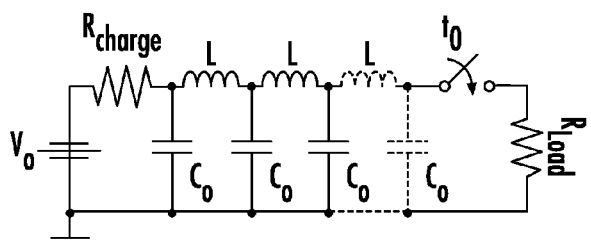
FIG. 7a is a schematic of a Transmission line-type PFN.
Figure 7B:
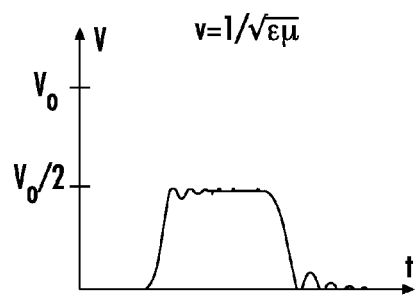
FIG. 7b is an example of a waveform for a Transmission line-type PFN.
Figure 8A:
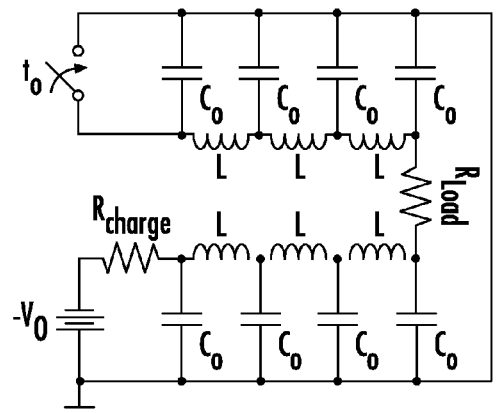
FIG. 8a is a schematic of a Blumlein line-type PFN.
Figure 8B:
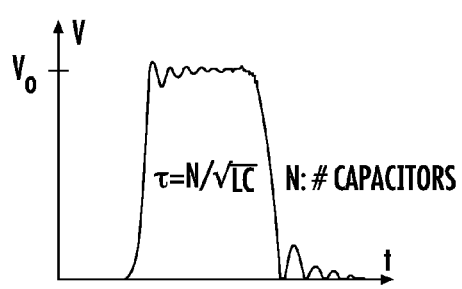
FIG. 8b is an example of a waveform for a Blumlein line-type PFN.
Figure 9:
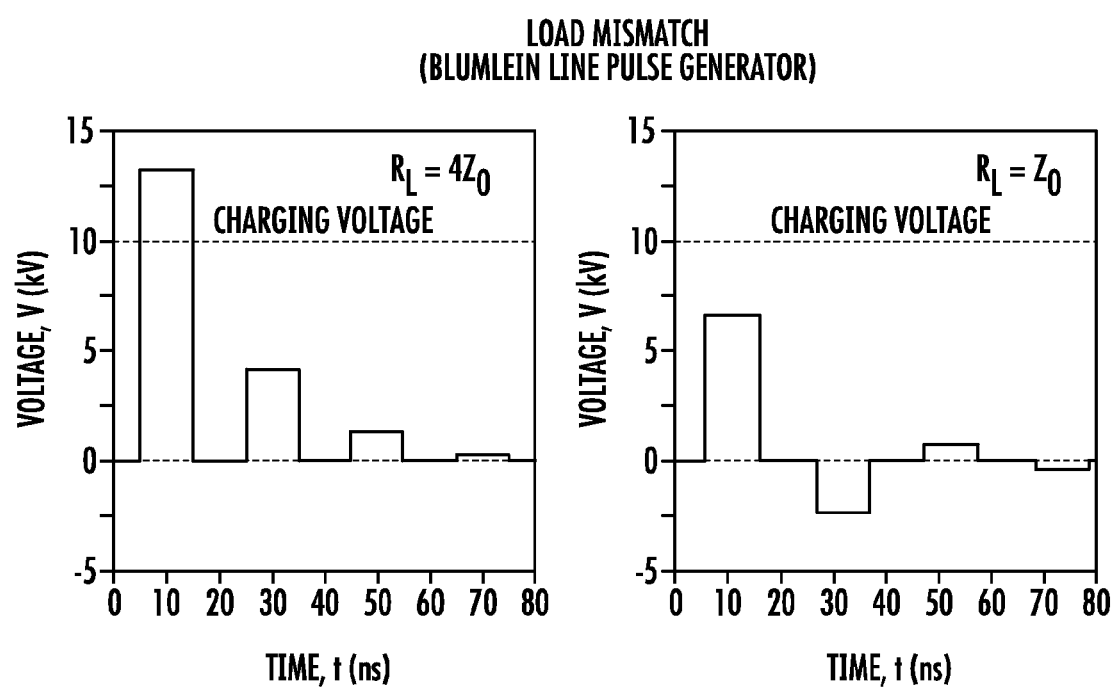
FIG. 9 is shows a chart of the voltages for a mismatched Blumlein line-type PFL.

The pulse generator can be a pulse generator selected from the group consisting of a Blumlein line-type Pulse Forming Line (PFL) pulse generator (e.g., as shown in FIG. 6a), a Blumlein line-type Pulse Forming Network (PFN) pulse generator (e.g., as shown in FIG. 8a), a Transmission line-type PFL pulse generator (e.g., as shown in FIG. 5a), and a Transmission line-type PFN pulse generator (e.g., as shown in FIG. 7a). Of course, variations on these generators are envisioned.

The system can be designed such that a source impedance of the pulse delivery system is less than or equal to the impedance of a target tissue. When the impedance is mismatched, a train of pulses with exponential decaying amplitudes will be delivered instead of a single pulse. This can be used advantageously for application of both tissue conditioning and spark pulses. As shown in FIG. 1, the system 10 can also include a resistor 38 placed in parallel to the gap between the electrodes 14, 16 (i.e., where the target tissue will be located) in order to control the impedance of the system 10 relative to the target tissue. For example, as shown in FIG. 1, the resistor 38 can be connected in parallel between a first connector 37 in electrical communication with the first electrode 14 and to a second connector 39 in electrical communication with the second electrode 16. This technique can be used to control the impedance of the system 10 to achieve the desired matched or mis-matched condition.

The invention is also drawn to a method of transmitting a spark through tissue. The method can be stored as machine executable instructions on a computer readable storage device 28 and can include contacting at least two electrodes 14, 16 having sharp surface features with target tissue and then delivering a plurality of pulsed voltage differences between said at least two electrodes 14, 16. The pulsed voltage differences producing a voltage difference can range from about 0.5 kV to about 100 kV for a duration of about 1 ns to 30 µs. The method can also include determining whether at least one of the pulsed voltage differences produced a spark between the electrodes 14, 16. As used herein, contact is used to include contact with a surface of tissue, such as skin, and contact with subcutaneous tissue, such as where a needle electrode penetrates a tissue surface.

The method can also include monitoring the current or voltage produced while the plurality of pulsed voltages differences are delivered, and determining whether a spark was produced by comparing the detected current or voltage to a predetermined threshold value associated with spark formation. Once a spark is detected, the tissue conditioning phase is complete and the sparking phase can begin. The sparking phase can include applying a predetermined number of additional pulsed voltage differences to the at least two electrodes 14, 16. The voltage difference, duration or both of the additional pulsed voltage differences can be different from those of the plurality of pulsed voltage differences.

Spark Discharge Mechanism

A spark discharge results from the electrical breakdown of a dielectric, which can be a gas, liquid or solid. The spark discharge process describes the transient formation of a highly conductive channel through a dielectric from a first electrode to a second electrode. A spark is initiated when the electric field across the dielectric exceeds a threshold strength and unbound seed electrons are accelerated enough to generate more free (and subsequently also accelerated) electrons in collisions with molecules and atoms of the dielectric medium. Once this electron avalanche has bridged the potential difference that was responsible for the original electric field, a high current through the now established conductive connection leads to rapid equilibration of the original potential difference between the electrodes. In this process the energy that was originally stored in the electric power source responsible for the supplied voltage, is dissipated in the plasma channel produced by the conductive connection. Since the energy for the spark is not continuously supplied to sustain the current, the spark discharge eventually extinguishes. This can be contrasted with an arc discharge, where the current is sustained.

A generic method to apply an electric field to a dielectric, e.g., tissue, is through electrode configurations of at least two separate electrodes. In general, at least one of the electrodes is biased with a high voltage and at least one other electrode is kept at a different reference potential, e.g., ground potential. The second electrode can either be defined in the electrode configuration or it can be assumed by auxiliaries (such as support structures).

The initiation of a spark discharge requires that the electric field exceeds the dielectric strength of the dielectric so that a conductive channel can bridge the potential difference and electrically connect the respective electrodes. In comparison, corona discharges and streamer discharges do not need to electrically connect electrodes. Accordingly, the initial electron avalanche and therefore the formation of a conductive channel, originates from the region of highest electric field strength and progresses from there towards the next electrode as long as the electric field can sustain the avalanche mechanism.

Electrode Configuration

The electric field distribution is controlled by the geometry of the electrodes. The field is enhanced at smaller curvatures, i.e., sharp surface features, such as sharp tips or edges, and along the shortest distance between electrodes. Electrode configurations can be designed accordingly to promote a spark discharge along a specific path in this geometry.

In some embodiments, as shown in FIG. 1, a portion of a surface of at least one of the at least two electrodes 14, 16 can be covered with a dielectric material 34. Similarly, a portion of each of the at least two electrodes 14, 16 can be covered with a dielectric material 34. As shown in FIG. 1, a proximal portion (i.e., the portion closes to the electrode hear 12) of a surface of at least two of the at least two electrodes 14, 16 can be covered with a dielectric material 34, while the distal portion, which includes the sharp surface features 18, is free from a dielectric material. Although sparks tend to propagate from a sharp surface feature 18 to sharp surface features 18, the use of a dielectric coating 34 can help enhance the localization of the spark at the sharp surface features 18.

A number of different exemplary electrode configurations shown in FIG. 11a-f are described below:

As shown in FIGS. 11a, 11b, 11c and 11d, the electrodes 14, 16 can include needle tips. In the embodiment of FIG. 10a, the electric field is enhanced at the sharp surface feature 18 of the electrodes 14, 16.

Figure 11A:
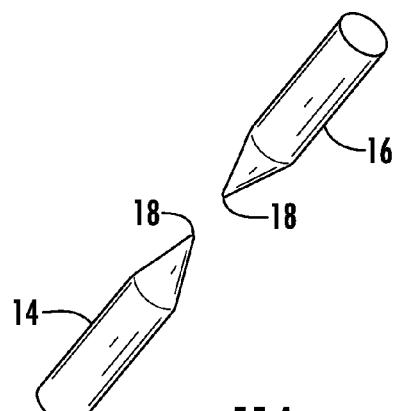
FIG. 11a shows a 2-needle electrode system.
Figure 11B:
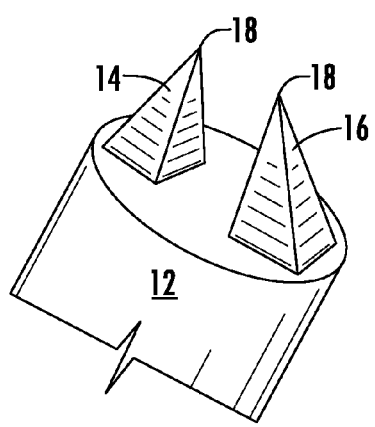
FIG. 11b shows an adaptation of a 2-needle electrode system.

FIG. 11b shows an adaptation of a two-needle electrode system of FIG. 11a. The electric field is highest at the sharpest tip 18. This is especially true if the tips also define the shortest distance between the electrodes. The overall dimensions can be kept small enough to integrate this electrode assembly, or the others described herein, onto the end of a catheter.

Figure 11C:
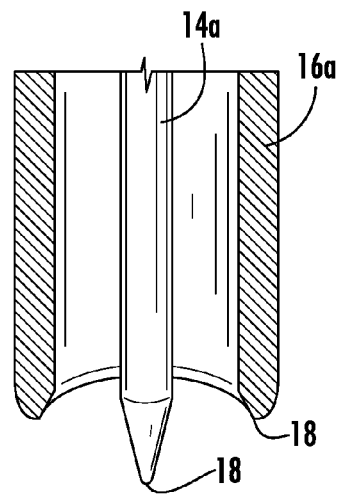
FIG. 11c shows a coaxial electrode arrangement.

As shown in FIG. 11c, the electrodes 14, 16 can include a ring electrode 16a and a needle electrode 14a extending beyond a distal end of the ring electrode 16a. The ring electrode 16a and the needle electrode 14a can be arranged coaxially. The electric field is highest at the tip 18 of the needle 14a. Sparks formed using this arrangement take random paths from the tip 18 of the needle 14a towards the edge 18 of the ring electrode 16a. The path is determined by the microstructure of the sharp surface feature 18 of the ring electrode 16a and the dielectric properties of the medium filling the spaces between the needle electrode 14a and ring electrode 16a. This electrode configuration is particularly suitable to ablate larger tissue volumes. In some embodiments, the system 10 can provide for rotation of the ring electrode 16a.

Figure 11D:
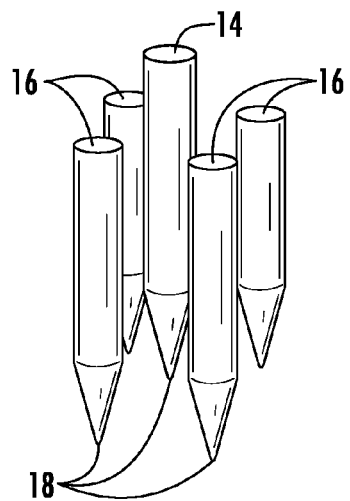
FIG. 11d shows a needle array with a biased high voltage needle electrode at the center.

FIG. 11d shows a needle array with a biased high-voltage needle electrode 14 at the center. The field is enhanced at the tips 18 of the individual surrounding needles 14, 16. A breakdown, e.g., a spark, can occur between the tip 18 of the center electrode 14 and the tip 18 of one of the surrounding needle tips 16. For symmetric conditions, sparks can be instigated toward individual surrounding needles 16, e.g., by slight changes in distance to the center needle. For example, the center needle 14 can be vibrated to change the distance between the center needle 14 and the variety of surrounding needles 16.

Figure 11E:
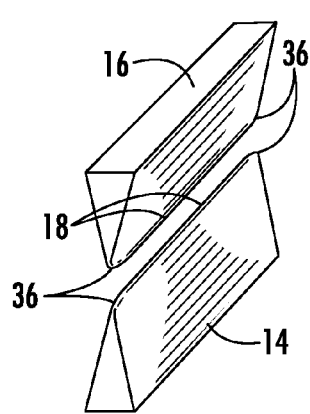
FIG. 11e shows a pair of parallel edge electrodes.
Figure 11F:
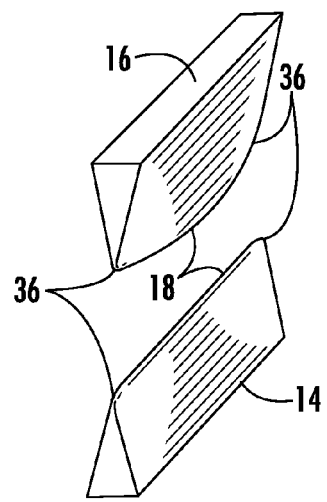
FIG. 11f shows a pair of electrodes with one curved electrode and one straight electrode.

As shown in FIGS. 11e and 11f, the electrodes 14, 16 can include edges and the at least two edges can be arranged in parallel. FIG. 11e shows a pair of parallel edge electrodes 14, 16 with rounded off corners 36. Sparks can originate at random from different locations along the edges 18 of the electrodes 14, 16. The location of the sparks can be determined by the microstructure, e.g., defects, of the edges 18. In addition, sparks can change the microstructure of the edge 18 causing subsequent sparks to originate from a different location. Similar to a needle array, multiple edge electrodes can be integrated onto the end of a catheter.

FIG. 11f shows a pair of edge electrodes 14, 16 with one electrode 16 with a curved edge 18 and one electrode 14 with a straight edge 18. The electric field is enhanced along the shortest distance between the electrodes 14, 16.

Many of these electrodes can be inserted through the skin with minimal damage to the skin and can easily target a tissue volume several tens of millimeters under the skin or inside an organ.

Mechanisms of Tissue Damage

The conductive channel that connects the electrodes initially (the connecting spark) is believed to be of a diameter that is on the order of a few tens to a few hundred micrometers. This value is derived from comparable observations of corona discharges in air and water. Prior to formation of the channel, i.e., electrical connection, the current through the channel is small (e.g., several hundred microamperes) and usually will not exceed a few milliamps. However, once the electrical connection is established, it provides a low resistive path and the current almost instantaneously increases to several tens to hundreds of amperes. The associated flow of energy leads to rapid evaporation in the channel, the generation of a thermal plasma in the channel and, simultaneously, an explosive expansion of the channel in the radial direction. Consequently, cells are destroyed along the way through evaporation and in the periphery of the thin conductive spark channel by the expanding shock front.

It should be noted that spark discharges in air and water have been shown to give rise to acoustic waves (i.e., the shockfront) that detach from the expanding plasma channel at the speed of sound. Close to the plasma channel, the pressure can reach several hundred atmospheres at the shockfront. However, the pressure decreases rapidly within a distance of only a few millimeters of the plasma channel to values that are comparable to the ambient pressure in the medium. The spark is produced by the discharge of the potential difference between the electrodes, i.e., by the energy that is stored in the system.

By controlling the energy in the system, the expansion and the associated tissue damage can be controlled. Cells and portions of tissue will only be destroyed by the expanding shockfront (acoustic front) as long as the energy per area, which is carried by this shockfront, or the corresponding pressure, is sufficient to disrupt the cells. The pressure decreases rapidly with the radial expansion and, from a certain distance onwards, the tissue will no longer be damaged due to the front. With the appropriate choice of electrode configuration and electrical parameters to generate the spark, the tissue damage can be limited to a volume that is on the order of 1 millimeter or less. Sustained damage may be caused by repetitive sparks though the same volume. In addition, by discharging a higher energy in a single pulse, the damage may be expanded.

To maximize the energy input into the shockwave, it is preferred that the electrical potential difference between the electrodes be established by high voltage pulses with fast rise times. In comparison, slower rising pulses will lead to a less explosive expansion and relatively higher dissipation of energy in resistive heating (Joule heating) of the tissue.

Of particular interest, the damage to the tissue by the spark discharge is not primarily caused by burning the tissue. In this respect, the method differs from other electrosurgical methods that use a continuous current to cauterize the tissue. For the most common prior art technique, the current is commuted either by direct contact of the electrode with the tissue or through a plasma layer between electrode and tissue. The plasma can be considered a (sustained) thermal arc, although it only spans the short distance between electrode and tissue. The tissue, e.g., the body, is usually the second electrode. Often an electrolyte, e.g., a saline solution, is added as a conductor between electrode and tissue. No shockwaves are generated by this process.

A second alternate prior art technique utilizes a glow discharge which is sustained by a continuous current between two or more electrodes. The tissue damage is presumed to be caused by chemical reactions of the radicals that are generated in a glow discharge with the tissue. The glow discharge plasma fills an extended volume and again the damage is not mechanically caused. Burned tissue is observed as a side effect.

While in both prior art cases the plasmas are sustained for seconds or minutes with currents of several milliamps to amps and voltages as high as a few hundred volts, the spark-discharge plasma disclosed herein is highly transient, lasts only fractions of a millisecond, carries currents of several hundred amps and, for electrodes spaced a few millimeters apart, requires application of voltages in the kilovolt range. Thermal damage to the target tissue is produced along the core of the discharge (i.e., spark) channel, however, the effect is superseded by the rapid expansion, which damages the tissue in a larger, although well defined and local volume. Further, the spark discharge is generated in the tissue itself and does not require adding a conductive liquid to enable a discharge/current.

Pulse Delivery System

A breakdown in the tissue, i.e., a spark, is initiated when a high enough voltage is applied to the electrodes of the delivery system for a long enough duration to overcome the dielectric strength and impedance of the tissue. To avoid tissue damage by Joule/Ohmic heating, it is desirable to achieve a breakdown quickly, i.e., prior to any other sustained period of current flow. In cases where a spark occurs, it is advantageous to limit the energy that is dissipated in the tissue. This way the tissue damage can be controlled and regulated.

The constraints on the electrical parameters can be observed by the application of pulsed high voltages of short duration. Pulse amplitude and duration depend on the electrode configuration and tissue properties, but in general, amplitudes of several kilovolts (typically 10-20 kV) and durations of not more than a few microseconds (typically several hundred nanoseconds) suffice. However, amplitudes in the range of 0.5 kV-100 kV and durations of 1 ns-10 µs may also be used.

Pulses having these specifications can be provided by different electrical circuits, such as those shown in FIGS. 5-8. A generic way to generate a high voltage pulses is with a capacitive discharge. When the discharge circuit through the load is closed by a fast closing switch, the charging voltage of the capacitor is applied across the tissue. During the capacitive discharge, the voltage has to be kept above the breakdown voltage long enough to initiate a spark. For known tissue impedance, this time can be adjusted by the value of the capacitor or a much higher than necessary charging voltage. The energy that is stored in the system and delivered with the spark is determined by the charging voltage and the capacitance.

A variation of the capacitive discharge uses an inductive component in series with the load. In this RCL-circuit, inductive overshoots can provide transient voltages across the load that can be higher than the charging voltage of the capacitor. An alternative concept can use the under-damped (oscillating) conditions of an RCL-discharge circuit to apply a train of short high voltage spikes.

A way to generate well defined pulses with respect to pulse duration and amplitude is by means of a transmission line circuit. This concept (and its derivatives, such as Blumlein lines, pulse forming networks, Guillemin networks, etc.) can generate a single, ideally rectangular pulse. The pulse generator can be designed with respect to the impedance of the tissue and to store a specified energy, which is then delivered during a breakdown. By deliberately 'mismatching' the system (i.e., mismatching the impedance of the pulse generator and the impedance of the load that is connected to it), a train of pulses can be generated with amplitudes that are chosen to be either higher than or lower than the charging voltage.

Several pulse generator concepts are summarized in FIGS. 12($a$)-($c$). In the graphs in FIG. 12($a$)-($c$), $V_o$ represents the initial voltage, $V_b$ represents the estimated breakdown or spark voltage, and $R_L$ represents the resistance of the load, i.e., the target tissue. The list is by no means comprehensive and can include other variations, such as those shown in FIGS. 5-8. In addition, other concepts, such as a Marx bank circuit, can also be employed to provide high voltage pulses that can lead to a spark.

FIG. 12$a$ shows a capacitive discharge circuit and a graph of the voltage starting when the switch is closed (at time $t_0$). The time constant (RC-time) can be adjusted to provide conditions leading to a spark in the tissue.

FIG. 12$b$ is a RCL discharge circuit and a graph of the voltage starting when the switch is closed (at time $t_0$). In the chart, $d_p$ represents the pulse duration. The circuit provides oscillating high voltage "pulses." Both polarities can lead to breakdown.

FIG. 12$c$ is a transmission line circuit generating a rectangular pulse and a graph of the voltage starting when the switch is closed (at time $t_0$).

Tissue Conditioning

The dielectric strength of a medium, or for a given electrode geometry the corresponding breakdown voltage, can be considered a material constant (within narrow statistical margins of a few percent). However, this constant depends on the time a voltage is applied and on ambient conditions.

Figure 13B:
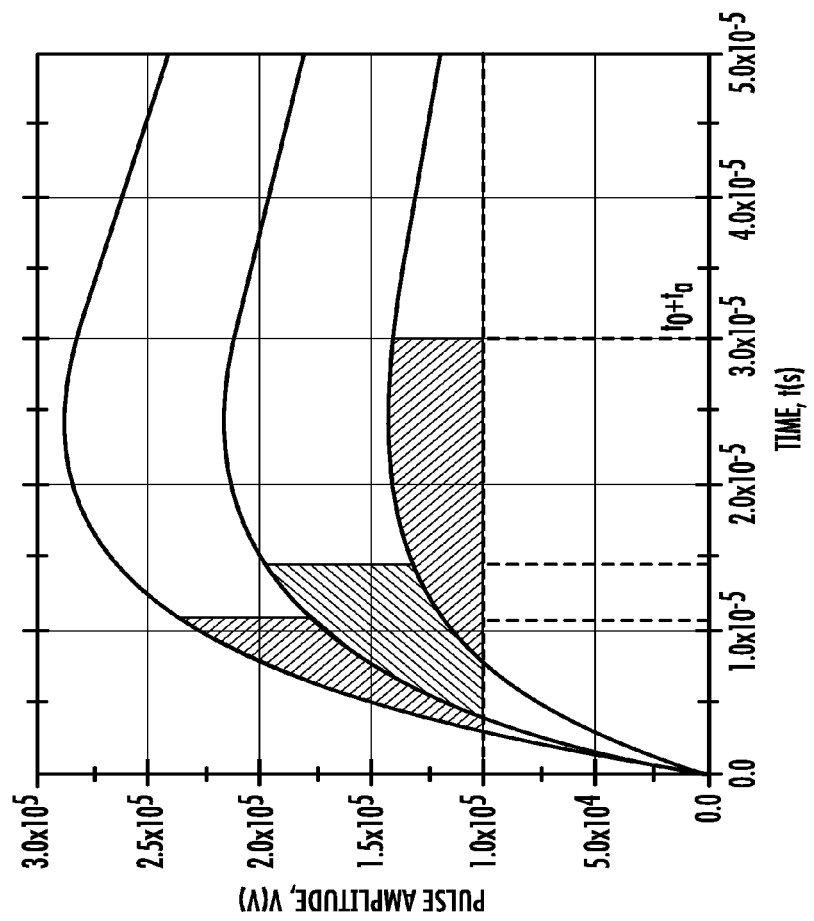
FIG. 13b illustrates the increase in breakdown voltage for the application of pulsed voltages.
Figure 13A:
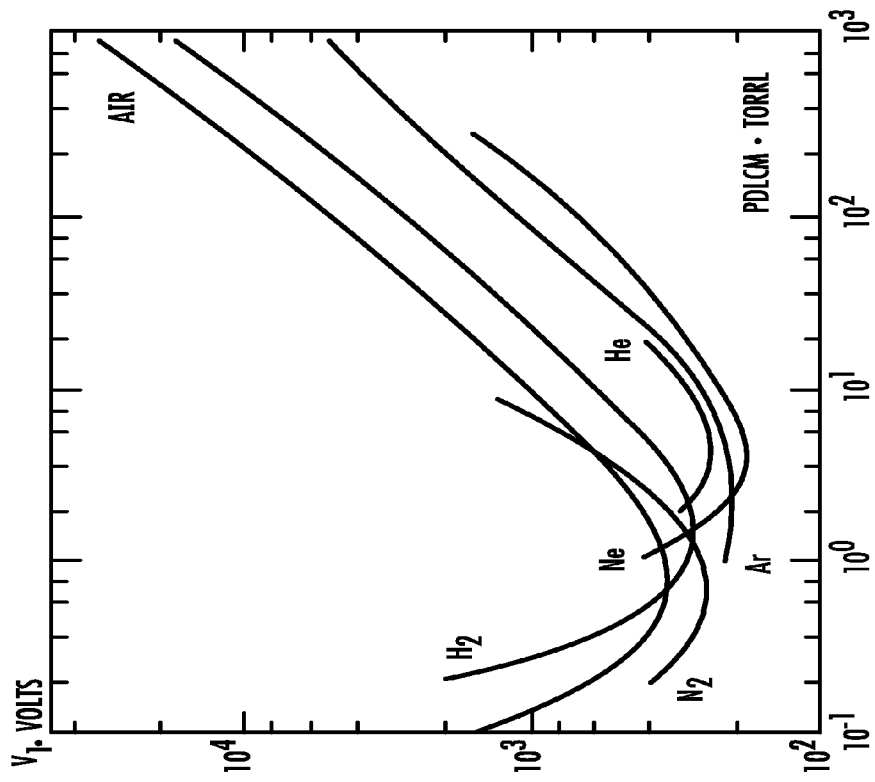
FIG. 13a shows Paschen curves for different gases for the application of a dc voltage in a homogenous electric field.

The breakdown voltages of gases are for dc voltages are determined by the product of gas pressure and electrode distance using Paschens' law. For example, as shown in FIG. 13(a), the breakdown voltage for air at atmospheric pressure, in a homogeneous electric field with an electrode distance of 1 cm, i.e., without field enhancement, is 30 kV, corresponding to a dielectric strength of 30 kV/cm. As shown in FIG. 13(b), the dielectric strength is significantly higher for pulsed voltages. Depending on electrode geometry and pulse duration, values for the dielectric strength under pulsed electrical stress are commonly determined empirically.

Figure 14:
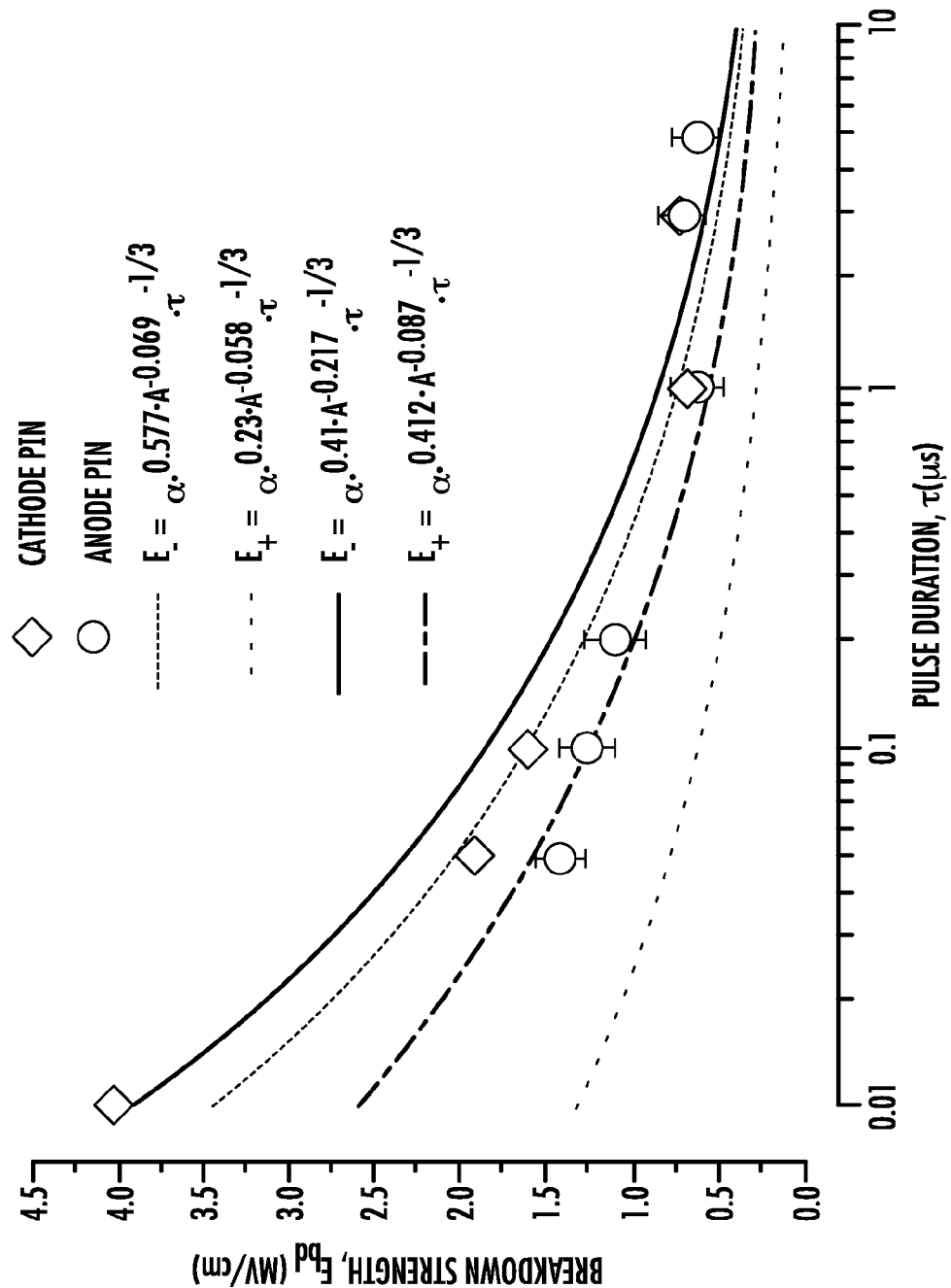
FIG. 14 is a graph showing experimental values and simulation predictions for the application of rectangular pulses between a pin-electrode of a 0.8 mm tip radius and a flat electrode in 200 µm distance.

Liquids and in particular insulating liquids have a much higher dielectric strength than gases. Semi-empirical formulas taking into account electrode configuration and pulse duration have been found by J. C. Martin and Kolb, et al., among others. For example, FIG. 14 is a graph showing experimental values and simulation predictions for the application of rectangular pulses between a pin-electrode having a 0.8 mm tip radius and a flat electrode in 200 μm distance. For a 200-ns electric pulse applied to water, the dielectric strength is on the order of 1 MV/cm.

Solids are known for dielectric strengths that far exceed values of liquids, in particular polar liquids, such as water. Data on pulse breakdown voltages for pure materials is scarce, since the extremely high values are usually of little practical relevance.

The breakdown voltage for different media was assessed experimentally using two acupuncture needles of 0.4 mm in diameter as electrodes. The tips of the acupuncture needles were aligned with tips facing each other a distance of 7 mm apart. Electrical pulses 320 ns in duration were applied using a matched Blumlein line-type pulse forming network. In air at atmospheric pressure breakdown could be observed with pulse amplitudes as low as 5-7 kV. In tap water no breakdown could be observed with voltages of up to 25 kV. When the electrodes were inserted in excised adipose pig-tissue, a spark breakdown was achieved after the application of several pulses with an amplitude of 12.5-15 kV.

The result shows that the breakdown voltage for tissue is lower than that of solids or liquids, but still considerably higher than for gases. The results also show for biological tissues, the breakdown voltage can be modulated using tissue conditioning pulses. In particular, the application of an electric field to the tissue changes the dielectric properties in a way that reduces the dielectric strength of the tissue. This is in direct contrast to typical homogeneous media (gases, liquids, solids), where the breakdown voltage is constant for a given electrode geometry and pulse duration at ambient conditions.

Conditioning of tissue can be achieved with the same pulses that are used to initiate a spark breakdown. Depending on the duration and amplitude of the pulses, different numbers of tissue conditioning pulses can be required before breakdown can be achieved. There is a limit to the reduction in dielectric strength so no spark breakdown is observed if the pulse amplitude is too low or the pulse duration too short. Alternately, tissue conditioning can also be achieved with pulses with specific parameters that differ from the pulse that is used to initiate a spark. The tissue conditioning can be observed by a decrease of the tissue impedance in the exposed volume. While the particular details of the associated tissue modifications are not yet understood, because a decrease of the impedance alone does not explain the reduced breakdown voltage, the exact mechanism is not for practicing the invention.

DETAILED DESCRIPTION OF PREFERRED EMBODIMENTS

In one embodiment of the invention, to achieve the plasma spark, partially insulated needles are inserted through the skin and into the particular tissue. Though this arrangement is described, other arrangements are also possible. Should the tissue being treated be that of an internal organ, such as a lung, liver, or kidney, a catheter can be used to gain access to the organ.

Pulses are applied at a certain repetition rate. The repetition rate may be in the range of 0.5 Hz to 100 Hz though other rates are also possible. Pulses at these rates are considered independent from one another since the plasma spark duration is much shorter than the interval between adjacent pulses. In other words, there is no residual plasma from a first spark in the target volume by the time the next spark is formed. This technique, therefore, is different than, for example, the pan plasma processes that uses higher frequencies. Also, because of this difference the tissue heating effects are small because the frequency allows for diffusion of heat.

Figure 2:
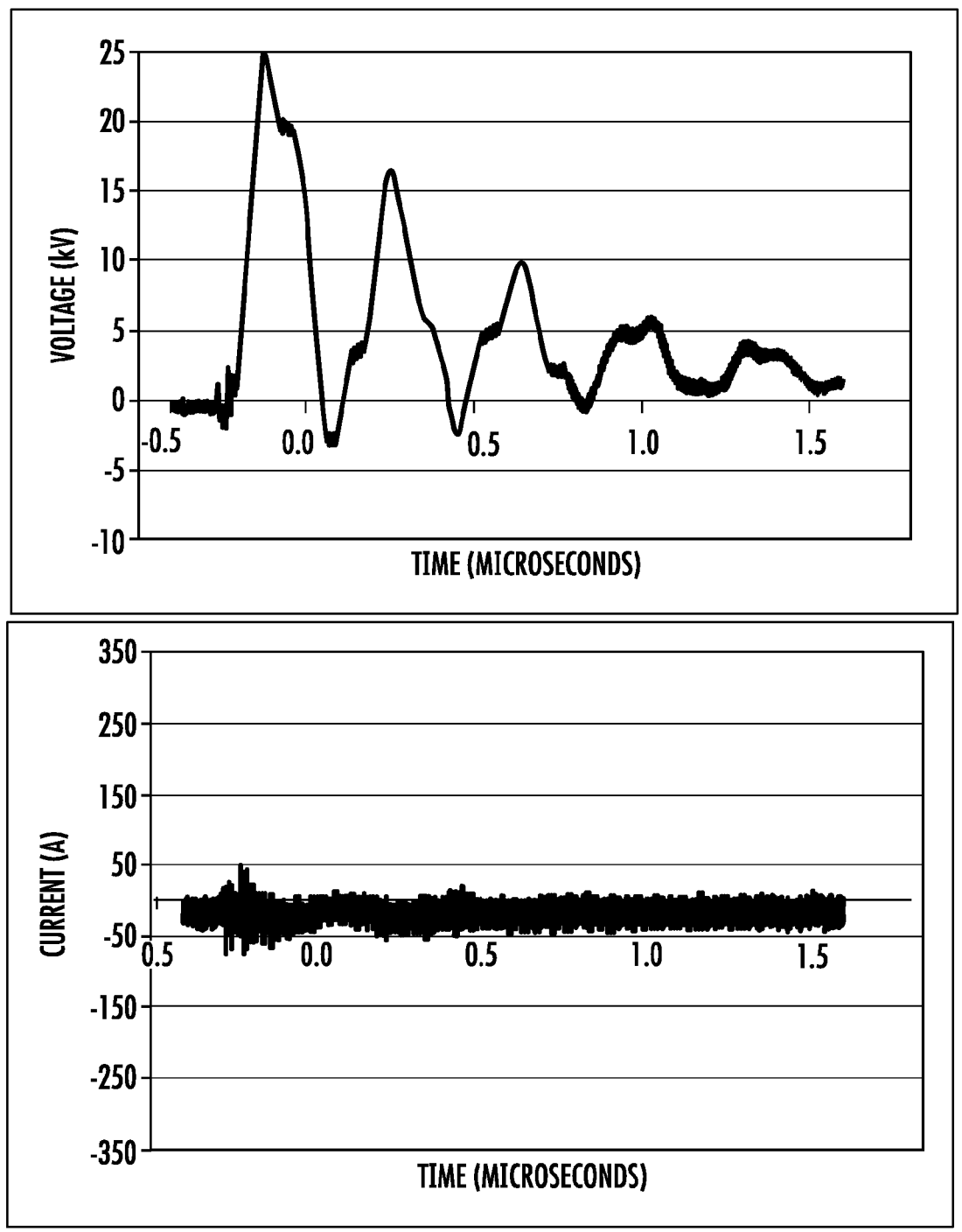
FIG. 2 shows example waveforms in pre-plasma tissue conditioning pulses.

The pulses typically have a voltage of between 2.5 kV-35 kV, and are typically applied for duration in the range of 50 ns-1000 ns. However, at times the pulses may have a voltage ranging between 0.5 kV-100 kV and may be applied for duration in the range of 1 ns-10 μs. Typically, the source impedance of the pulse generator is less than or equal to the impedance of the tissue. At first, pulses may not always lead to a spark. However, such pulses serve to condition the tissue to facilitate subsequent spark formation. During the pre-plasma tissue conditioning pulses, energy is introduced into that tissue thereby altering the tissue characteristics in the exposed volume adjacent and between the electrode needles. This leads to increasing current (through tissue) as tissue conditioning proceeds and a corresponding reduction in tissue impedance. Example waveforms for pre-plasma tissue conditioning pulses are show in FIG. 2.

Figure 3:
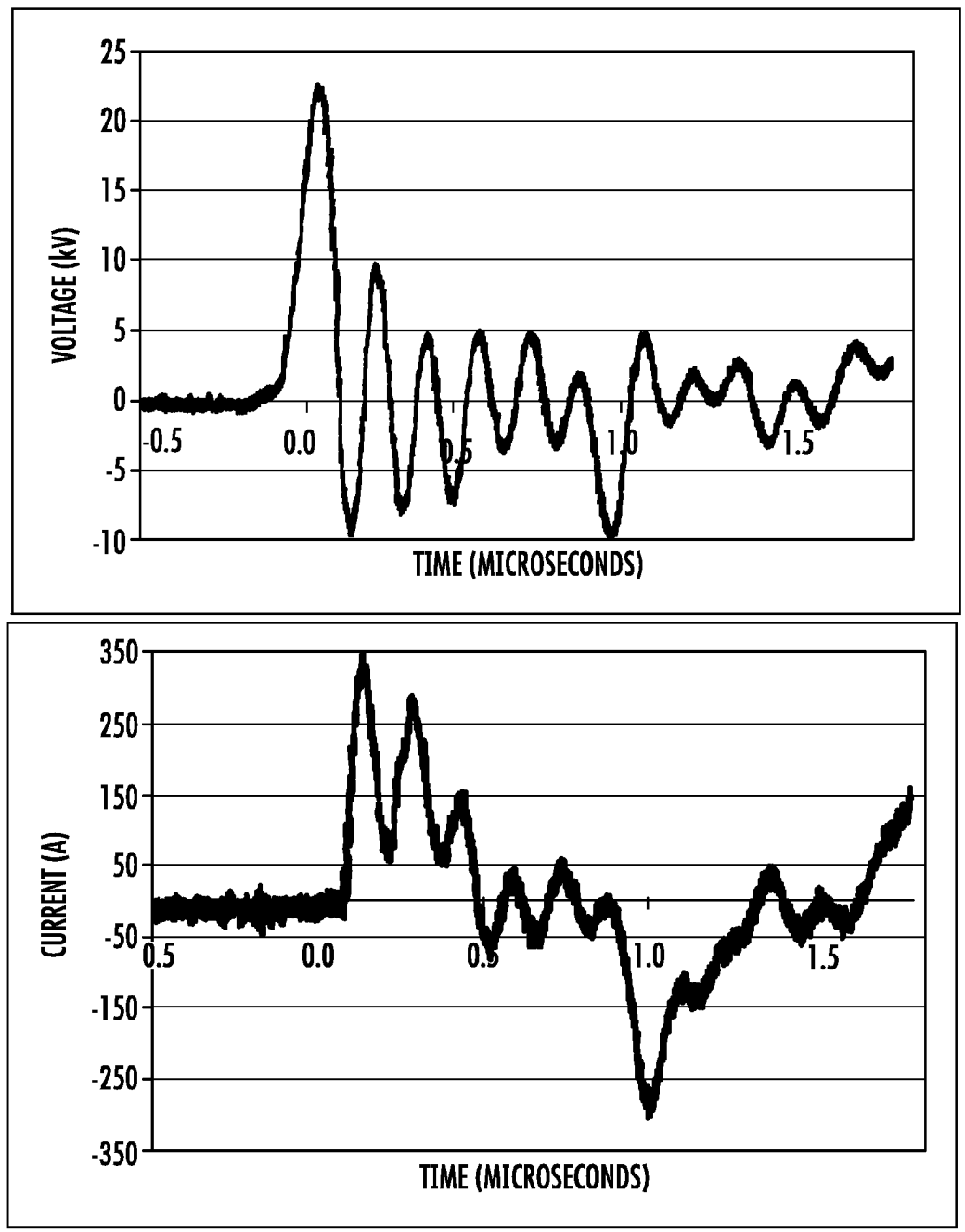
FIG. 3 is shows example waveforms for a plasma pulse.

If the pulse amplitude is high enough with respect to the impedance and dielectric strength of the tissue to which it is applied a plasma spark, also termed as tissue breakdown, occurs in the tissue. The tissue principally affected by the spark is the volume between the exposed electrode needle parts. Example waveforms for a plasma pulse are shown in FIG. 3.

Figure 4:
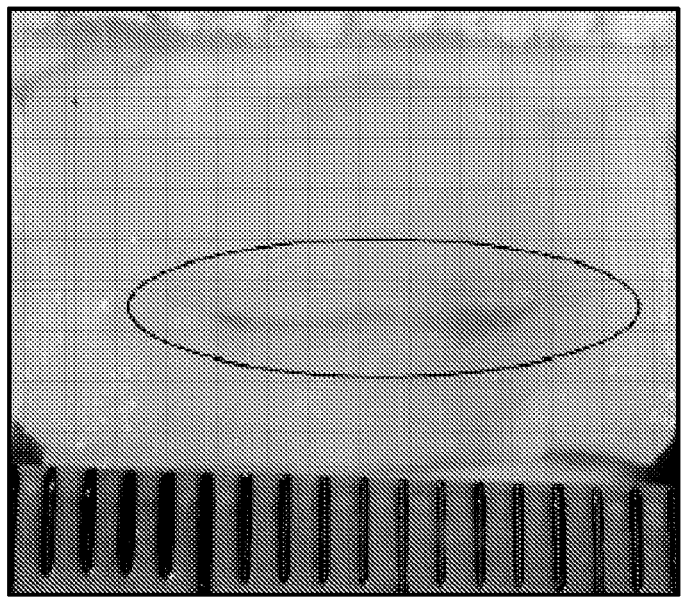
FIG. 4 is a cross-sectional view, perpendicular to the needle plane through the location of needle tips, of pig fat tissue after plasma treatment.

Observed tissue damage can be nearly linear or filamentous or s-shaped in a channel. A picture of a plasma spark cut is shown in FIG. 4. Additional pulses may be delivered after the first plasma spark formation. In comparison with tissue conditioning pulses, breakdown or plasma pulses are characterized by much higher current, flashes of light emanating from the plasma volume, and mechanical shock-waves.

Subsequent pulses applied after the first breakdown will be principally plasma or breakdown pulses though they may be interspersed with some non-plasma pulses. The pre-breakdown (tissue conditioning) pulses, with no plasma effect, will eventually lead to apoptosis of adipocytes as described in U.S. Pat. No. 5,561,348. In the treatment of cellulite, the post-breakdown pulses with plasma cutting will lead to significant disruption of fat cells and cutting of the intervening septae. Either of the two effects or a combination will lead to the desired effect of treating cellulite.

Thus, in some embodiments, the device and method can be used for non-therapeutic treatment of cellulite. In such methods, the electrodes can be inserted into subcutaneous tissue and the sparks used to cut septae in the fatty tissue. The end result of this cosmetic method is the elimination or reduction of the bumpy appearance of the skin.

It is believed that the number of pulses required to achieve breakdown is dependent on the voltage of each of the pulses, on the tissue being treated, and on the individual patient. For example, when the pulse amplitude is increased, the number of pre-plasma tissue conditioning pulses that must be applied to create a plasma spark decreases. However, the number of pulses required to create a plasma spark also depends on the tissue impedance of the type of tissue and may vary from patient to patient and location to location on the same patient. This is especially true for large organs, such as the skin.

Generally, however, at low voltages, a high number of pulses are required while at high voltages, a smaller number of pulses are required. It is possible though that at low enough voltages, the number of pulses required would be too high to be practically useful. In the case of a Blumlein line-type PFL or PFN (as shown in FIGS. 6 and 8, respectively), the total energy delivered during plasma pulses is proportional to the total number of plasma pulses. The energy per pulse is calculated as ½ times total capacitance of the Blumlein line-type PFL or PFN and square of the input charging voltage.

Upon plasma formation, almost 100% of the stored energy is delivered into tissue. Thus, the total energy coupled into tissue can be controlled by choosing the capacitance, voltage and the number of plasma pulses. The number of plasma pulses can be controlled by the operator by using diagnostics to discriminate between the non-plasma and plasma pulses and based on an understanding of the tissue effect as a function of number of plasma pulses. Thus, the affected volume of tissue and magnitude can be well controlled by the choice of the capacitance, voltage and number of breakdown pulses. Whether a pulse is a tissue conditioning non-plasma pulse or a plasma pulse can be determined by monitoring the voltage and/or current versus time during the pulse. The characteristics of the voltage and/or current for a non-plasma and a plasma pulse are different enough to allow for reliable discrimination.

For example, as seen in FIG. 3, a plasma pulse is characterized by the breakdown of the voltage during the pulse, effectively shortening the time for the application of the voltage. Also, the plasma formation is followed by strong oscillations in current and voltage as they are characteristic for an RCL-discharge circuit. In comparison, for the matched cases non-plasma pulses are well defined, rectangular voltage pulses with a duration characteristic for the PFL/PFN and an amplitude that is equivalent to the charging voltage. Examples of non-plasma pulses can be seen in FIGS. 5*b*, 6*b*, 7*b* and 8*b*.

In one embodiment, the source impedance used is much lower than the tissue impedance across the needles. With this impedance mismatch, the voltage across the tissue can be as high as twice the input charging voltage. Having lower charging voltages has many advantages such as use of a simpler, less expensive, smaller, source. However, in the mismatched case, reflected pulses effectively extend the application of voltages across the tissue. To avoid these reflections, a resistor of appropriate value can be placed parallel to the tissue to generate a matched condition, reducing or eliminating reflections.

In another embodiment, the source impedance is close to the tissue impedance. This leads to a well-matched system and hence, minimal reflections.

As noted above, there is great variance in the impedance of different tissues. Accordingly, in some embodiments, where a mismatch is desired, a system can be designed according to the tissues being treated such that the source impedance of the system is lower than the lowest impedance of the tissues that would be treated.

In another embodiment, reflections are avoided by matching the Blumlein line-type pulse generator at one end. The shape of the voltage pulse across the load for any load a single, rectangular pulse, as expected for a matched case. The voltage amplitude depends on the ratio of the load resistance to the matching resistance. The pulse duration in a Blumlein line-type PFL or PFN is determined by the single transit time along the line (or network). For load resistances that are large compared to the PFL or PFN impedance, the voltage across the load approaches the full charging voltage. For the present system, if the voltage is less than the desired one, due to a lower than expected resistance of the load, the voltage can be up-regulated, and vice versa. Perfect matching at a given voltage can be achieved by adjusting the voltage at the power supply. There is no need to adjust any resistor.

One example of the apparatus used in the current invention shown in FIG. 8*a* includes a pulse forming network in a Blumlein line-type configuration that has two branches. Each branch has four stages with four capacitors (nominal value 0.67 nF) and three inductors (approximate value 2.0 micro-Henry). The values in this example are chosen so the source impedance is on the order of approximately 100 ohms. Also, in this example, the nominal pulse duration is on the order of 400 ns. Silicon insulated high voltage cables transmit the high voltage pulse to a handpiece that contains two microneedles used to deliver the electrical energy to the tissue. These microneedles are thin, rigid, partially insulated metal elements. In this example, the microneedles were 8 mm long with 6 mm insulation in the proximal part and 2 mm bare metal part at the distal end and had a diameter of 400 microns. The electrodes had a tip as the origin of the spark. In alternate embodiments, the spark can originate from a sharp edge, or the like. The applied voltage in this example was on the order of 15 kV. To deliver the energy, the circuit was closed by a spark gap switch. Such a switch can operate at high voltage with fast closing times of only nanoseconds. The voltage at which the spark gap closes can be controlled by the separation of the electrodes of the switch or the pressure in the chamber. It can also be a triggered spark gap with the trigger coming from a third electrode when the desired voltage is available across the spark gap. Typically, the spark gap can be operated in a self-breakdown mode. If desired, a triggerable spark gap can be used. Alternatively, different trigger concepts (e.g., trigatron, field distortion trigger) are known to those skilled in the art.

Example 1

Treatment of Cellulite

The area on skin that is affected by cellulite dimples or folds was identified by the clinician and, where desired, the clinician used a dermal marker to delineate the dimples. Electrodes, such as those shown in FIG. 10, made of conducting material such as metals and for example, 27G, were inserted into the tissue. Then, after selection of treatment parameters, pulses were delivered at a desired repetition rate, for example, 10 Hz. The proximal parts of the microneedles were insulated with a material that has a high voltage breakdown threshold, such as poly(p-xylylene) polymers sold by Para Tech Coating, Inc., under the PARYLENE trademark. The distal part is bare, i.e., uninsulated. Typically, the first few pulses acted as pre-plasma tissue conditioning pulses (example, 5-100 pulses), which changed the electrical characteristics of the tissue between the electrodes. This was evidenced by a decrease in resistance that ultimately resulted in conditions leading to spark discharge. The tissue conditioning pulses were followed by plasma spark discharge pulses between the uninsulated parts of the electrodes and lead to cutting, damaging or destroying of the adipose and connective tissue in the path of the spark. The connective collageneous tissue typically has much lower resistivity than adipose tissue and hence may be a preferred conduit for the plasma spark. The release of the septal connections between the dermis and the fascia is one of the factors leading to reduction in the dimple prominence. Thus, in some cases, the treatments reduced or eliminated dimples. Other factors also include cuts in adipose tissue, redistribution of adipose tissue in the cellulite skin, reducing the cellulite appearance.

Example 2

Cutting of Tissue

Figure 10:
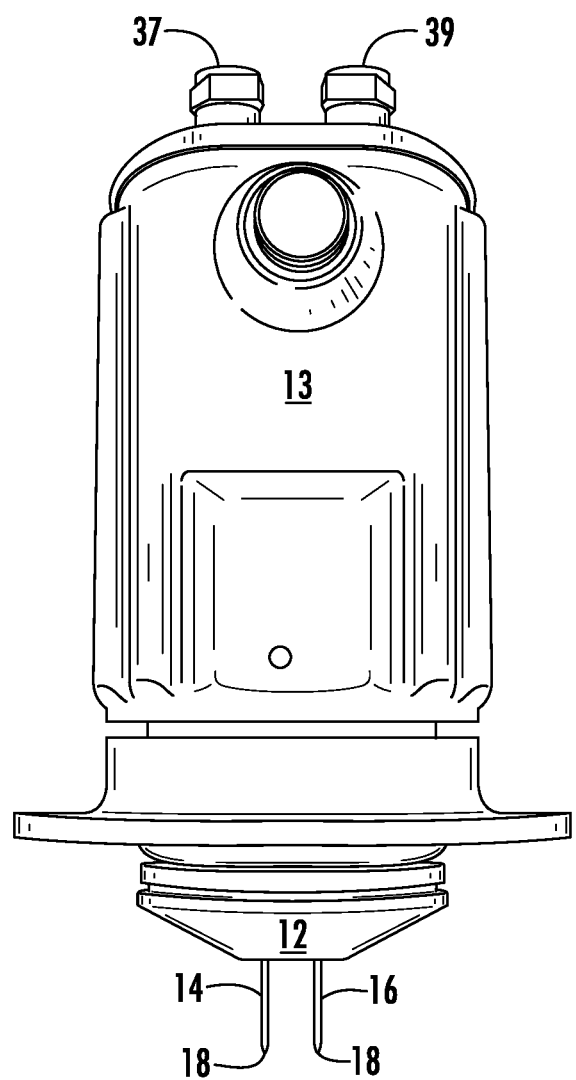
FIG. 10 is a picture of the electrodes in a handpiece assembly.

The adipose tissue of a pig was cut using the apparatus shown in FIG. 10 and method of the present invention. A picture of this cut is shown in FIG. 4. The individual marks on the ruler in FIG. 4 are 1 mm apart. This tissue cut was achieved using 0.40 J/spark delivered at 12.5 kV pulse voltage. Two partially insulated electrode needles, separated by 7 mm, were used. Eight (8) mm of the length of the needles were inserted into the tissue. Of the 8 mm length, the proximal 6 mm length of the electrode needles were coated with polyester insulation (other materials for insulation can also be used, for example, Parylene) and the distal 2 mm length were bare, i.e., uninsulated. The source impedance was 125 Ohm and the system was matched. The pulse duration was 327 ns. To cut the tissue, 34 pre-plasma tissue-conditioning pulses were applied followed by 20 sparks.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A pulse delivery system, comprising:
    at least two electrodes having sharp surface features, wherein the at least two electrodes are electrically isolated from each other and the sharp features of the electrodes are separated by a distance of about 2 mm to about 20 mm;
    a pulse generator in electrical communication with said at least two electrodes for delivering pulsed voltage differences between the at least two electrodes, said pulsed voltage differences producing a voltage difference ranging from about 0.5 kV to about 100 kV for a duration of about 1 ns to about 30 µs; and
    a controller in electrical communication with said pulse generator, said controller comprising a processor, a measurement device in communication with said processor and configured for measuring at least one of a voltage and a current for the at least two electrodes, and a computer readable storage device comprising machine executable instructions that, when executed, cause the processor to:
        generate control signals for causing said pulse generator to deliver a plurality of said pulsed voltage differences between said at least two electrodes, said plurality of pulsed voltage differences comprising conditioning pulsed voltage differences and treatment pulsed voltage differences different from said conditioning pulsed voltage differences in at least one of said voltage and said duration,
        determining whether at least one of said plurality of pulsed voltage differences produced a spark between said at least two electrodes by monitoring the at least one of the voltage or the current at the measurement device and determining that a spark was produced by comparing said at least one the voltage or the current to a predetermined threshold value associated with spark formation, and
        generating additional control signals for causing the pulse generator to apply a predetermined number of additional pulsed voltage differences to said at least two electrodes after said controller detects that at least one of said plurality of pulsed voltage differences produced a spark.

2. The pulse delivery system according to claim 1, wherein said current or voltage measuring device is selected from the group consisting of an ammeter, a multimeter, an oscilloscope, and a galvanometer.

3. The pulse delivery system according to claim 1, wherein a voltage difference, a duration or both are different for the plurality of pulsed voltage differences and the additional pulsed voltage differences.

4. The pulse delivery system according to claim 1, wherein said pulse generator is selected from the group consisting of a Blumlein line-type Pulse Forming Line (PFL) pulse generator, a Blumlein line-type Pulse Forming Network (PFN) pulse generator, a Transmission line-type PFL pulse generator, and a Transmission line-type PFN pulse generator.

5. The pulse delivery system according to claim 1, wherein a source impedance of the pulse delivery system is less than or equal to the impedance of a target tissue.

6. The pulse delivery system according to claim 1, wherein a portion of a surface of at least one of the at least two electrodes is covered with a dielectric material.

7. The pulse delivery system according to claim 1, wherein a proximal portion of a surface of at least two of the at least two electrodes is covered with a dielectric material.

8. The pulse delivery system according to claim 1, wherein said at least two electrodes are mounted at an end of a catheter.

9. The pulse delivery system according to claim 1, further comprising a resistor arranged in parallel with a gap between said sharp surface features.

10. The pulse delivery system according to claim 1, wherein said at least two electrodes comprise a ring electrode and a needle electrode extending beyond a distal end of said ring electrode.

11. The pulse delivery system according to claim 10, wherein said ring electrode and said needle electrode are arranged coaxially.

12. The pulse delivery system according to claim 1, wherein said at least two electrodes comprise edges and said at least two edges are arranged in parallel.

13. A method of operating a pulse delivery system comprising at least two electrodes electrically isolated from each other and having sharp surface features separated by a distance of about 2 mm to about 20 mm, a pulse generator in electrical communication with said at least two electrodes for delivering pulsed voltage differences between the at least two electrodes, the method comprising performing, via the controller, a controller in electrical communication with said pulse generator and having a processor, a computer readable storage device with instructions for controlling the processor, and a measurement device configured for measuring at least one of a voltage and a current for the at least two electrodes, the steps of:
    generating control signals for causing said pulse generator to deliver a plurality of said pulsed voltage differences between said at least two electrodes, said plurality of pulsed voltage differences comprising conditioning pulsed voltage differences and treatment pulsed voltage differences different from said conditioning pulsed voltage differences in at least one of said voltage and said duration;

determining whether at least one of said plurality of pulsed voltage differences produced a spark between said at least two electrodes by monitoring, via a measurement device, the at least one of the voltage or the current and determining that a spark was produced by comparing said at least one the voltage or the current to a predetermined threshold value associated with spark formation; and generating additional control signals for causing the pulse generator to apply a predetermined number of additional pulsed voltage differences to said at least two electrodes after said controller detects that at least one of said plurality of pulsed voltage differences produced a spark;

wherein said pulsed voltage differences are selected to produce a voltage difference ranging from about 0.5 kV to about 100 kV for a duration of about 1 ns to about 30 μs.

14. The method of claim 13, further comprising selecting at least one of a voltage difference or a duration to be different for the plurality of pulsed voltage differences and the additional pulsed voltage differences.

* * * * *